(12) United States Patent
Maynard

(10) Patent No.: US 11,654,323 B2
(45) Date of Patent: May 23, 2023

(54) MULTIFUNCTIONAL COMPUTERIZED ISOKINETIC STRENGTH TRAINING AND REHABILITATION SYSTEM

(71) Applicant: Alan William Maynard, North Haven (AU)

(72) Inventor: Alan William Maynard, North Haven (AU)

( * ) Notice: Subject to any disclaimer, the term of this patent is extended or adjusted under 35 U.S.C. 154(b) by 208 days.

(21) Appl. No.: 16/911,407

(22) Filed: Jun. 25, 2020

(65) Prior Publication Data
US 2020/0324158 A1   Oct. 15, 2020

(51) Int. Cl.
*A63B 21/002* (2006.01)
*A63B 21/00* (2006.01)
(Continued)

(52) U.S. Cl.
CPC ...... *A63B 21/002* (2013.01); *A63B 21/00069* (2013.01); *A63B 21/4035* (2015.10); *A63B 21/4049* (2015.10); *A63B 24/0062* (2013.01); *A63B 71/0622* (2013.01); *A63B 2071/065* (2013.01); *A63B 2071/0658* (2013.01);
(Continued)

(58) Field of Classification Search
CPC ..... A61B 5/1114; A61B 5/1121; A61B 5/221; A61B 5/224; A63B 21/00069; A63B 21/002; A63B 21/008; A63B 21/4029; A63B 21/4035; A63B 21/4047; A63B 21/4049; A63B 23/0211; A63B 23/025; A63B 23/03508; A63B 23/03525; A63B 23/0482; A63B 23/0494; A63B 23/1209; A63B 23/14; A63B 23/16; A63B 24/0062; A63B 71/0622; A63B 2701/065; A63B 2701/0658; A63B 2208/0209; A63B 2208/0233; A63B 2220/16; A63B 2220/56; A63B 2225/093; A63B 2225/20; A63B 2225/50; A63B 2230/06; A63B 2230/60; G16H 15/00; G16H 20/30
See application file for complete search history.

(56) References Cited

U.S. PATENT DOCUMENTS 4,889,108 A * 12/1989 Bond ............... A63B 24/00
                                                    482/901
4,905,676 A *  3/1990 Bond ............... G16H 40/40
                                                    482/901
(Continued)

*Primary Examiner* — Joshua Lee

(57) ABSTRACT

Presented is an Isokinetic exercise system having a base, a pedestal, a vertical member, a height adjustable vertical column for resting a rotary actuator on top, a resistance control valve unit with rotatable dials connected to the actuator, wherein the rotatable dials are selectively used to rotatably set a range of resistances for opposing movements to accommodate varying exerted forces by a user performing an intended exercise. The system further includes an electronics module to detect angle and pressure related data (as a measure of voltages) associated with the actuator, an A to D converter to convert the detected voltages in a digital form, a display unit embodying a program product for receiving, and processing the detected voltages to generate and display a muscular performance assessment report, store the received voltages for future comparison and enable printing the muscular performance assessment report, enable configuring next intended exercise.

18 Claims, 13 Drawing Sheets

(51) Int. Cl.
*A63B 24/00* (2006.01)
*A63B 71/06* (2006.01)

(52) U.S. Cl.
CPC ... *A63B 2208/0233* (2013.01); *A63B 2220/16* (2013.01); *A63B 2225/50* (2013.01); *A63B 2230/60* (2013.01)

(56) References Cited

U.S. PATENT DOCUMENTS

| | | | |
|---|---|---|---|
| 9,724,563 B2 * | 8/2017 | Schmidt | A63B 24/0062 |
| 10,328,307 B2 * | 6/2019 | Schmidt | A63B 21/002 |
| 10,946,245 B2 * | 3/2021 | Schmidt | A63B 21/002 |
| 11,331,536 B1 * | 5/2022 | Wood | A63B 23/085 |
| 2009/0124461 A1 * | 5/2009 | Pinto | A63B 21/4043 482/7 |
| 2016/0114211 A1 * | 4/2016 | Schmidt | A63B 21/154 482/8 |
| 2017/0304680 A1 * | 10/2017 | Schmidt | A63B 23/03525 |
| 2019/0262663 A1 * | 8/2019 | Schmidt | A63B 21/4035 |
| 2021/0205664 A1 * | 7/2021 | Schmidt | A63B 24/0062 |

* cited by examiner

MULTIFUNCTIONAL COMPUTERIZED ISOKINETIC STRENGTH TRAINING AND REHABILITATION SYSTEM

FIELD OF THE INVENTION

The present disclosure relates to strength training exercise equipments in general, and more particularly to a multifunctional computerized Isokinetic exercise system that provides independent resistance control to accommodate varying forces exerted by a user while performing one or more strength training exercises, and facilitates assessment, and recording of the user's muscular performance to ensure safety and successful rehabilitation of the user from injuries, pain, medical procedures such as surgeries, or other body imbalances.

BACKGROUND

Isokinetic exercises are strength training workouts and require a controlled environment so that joints and muscles do not get over loaded while performing workouts as opposed to static or isometric exercises and dynamic or isotonic exercises. As known, Isokinetic exercises are performed to contract muscles at a constant speed at a range of motion. Isokinetic exercises may be performed concentrically (where muscles shorten during contraction) or eccentrically (where muscles lengthen during contraction) as external forces are applied to the limbs. Isokinetic exercises are not very common and are used as special recovery, and rehabilitation aid. Since Isokinetic exercises are controlled form of exercises for muscles, it makes the Isokinetic exercises efficient for injuries, pain and recoveries or rehabilitation.

Performing Isokinetic exercises for rehabilitation or recovery require specialized equipments, which are designed to control the amount of strength the user exerts. Most Isokinetic machines which exist today are expensive, non-portable and usually not found even at well equipped gyms or fitness centers around us. The Isokinetic exercising machines are mostly found in use at specialized rehabilitation centers to assess muscular strength objectively and to improve muscular strength in the users. The reasons behind this are mainly, these conventional machines are bulky with high cost, and occupy large area to install. According to a research report, the total operating floor spaces required for these conventional machines differ from model to model. For example Cybex 6000 (floor-based dynamometer) requires about 120 square feet area to be installed whereas newer models such as Biodex System 4 Pro System 4 Quick Set require 32 square feet area to be installed. Additionally, these conventional Isokinetic machines may require prior training to be instituted to users (such as therapists or coaches) responsible for operating the machines.

Additionally, some inventors in the past have also proposed different types of Isokinetic exercising machines. U.S. Pat. No. 3,465,592 discloses an apparatus which will afford a direct read out of the dynamic force applied by the person exercising throughout the course of his movement. As discussed in this patent, the apparatus will afford a direct read out of the dynamic force applied by the person exercising throughout the course of his movement. Broadly speaking, the inventor in the patent describes a mechanical, hydraulic and electrical system that provide an Isokinetic characteristic. U.S. Pat. No. 4,565,368 discloses about an Isokinetic exercise and monitoring machine for use in exercising and evaluating an individual's back muscles. U.S. Pat. No. 6,402,667 discloses an Isokinetic exercise apparatus particularly designed for exercising lower section of human body specially legs. U.S. Pat. No. 7,717,824 discloses an Isokinetic rehabilitation apparatus that mainly uses a motor-driven pedal assembly, a pair of foot pedals and the at least one hand engagement element, all of these mounted onto a chassis which is selectively pivotable with respect to a base. U.S. Pat. No. 4,577,862 discloses an Isokinetic apparatus which allows a person to stress muscles while doing the specific movements applicable to a specific sport (such as golf).

With this presented background information, one can understand the benefits or use of the Isokinetic exercises. Also, it can be understood that solutions do exist in the past that allow users to perform Isokinetic exercises, however, they are either expensive, non portable, complex in their design, bulky, or centered around facilitating performing specific resistance exercises only

BRIEF SUMMARY

Accordingly, an objective of the present invention is to provide an Isokinetic exercise system which is versatile, relatively compact (requiring less space to install) and which can be readily set up, operated, disassembled and transported to other locations for on-site uses conveniently.

The invention unlike the prior art combines a number of novel features including a real time on-site monitoring and display of user's muscular performance while the user is performing exercises or optionally allow storage of the user's performance report for future retrieval. Additionally, the invention facilitates independent resistance control to accommodate varying exerted forces during exercises using a dual concentric variable dual chambered control valve with which the user is able to select resistance on a scale of 1-10 in both opposing movements as desired. Further, the invention discloses the proposed exercising system's attachment compatibility with different types of exercising attachments/handlebars in order to allow the users to perform a variety of Isokinetic exercises (related to lower body and upper body conditioning) including but not limited to neck exercise, chest exercise, shoulder related exercise, back exercise, abdominal exercise, hip exercise, thigh exercise, knee exercise, leg exercise, foot exercise, ankle exercise, elbow exercise, wrist and hand exercises. All of these make the proposed exercising system a perfect rehabilitation or recovery solution for the users having injuries, pain, or have gone through medical procedures such as surgeries.

Further, The Isokinetic assessment (assessment of muscular performance of the users) allows the clinician or therapists to make sure the resistance exercises being performed are both safe and reliable for the rehabilitating users.

Another objective of the present invention is to provide Isokinetic exercise system having ability to control injury-risk since system won't let the users push (e.g. designated exercising attachment/handlebar) harder than necessary while performing exercises. To achieve this, the users are able to set a certain speed, and resistance can be selectively varied (in opposing directions) against the applied force or torque.

Further objective of the present invention is to provide the Isokinetic exercising system that would be less expensive since the system would allow the users perform a multitude of exercises using same machine by just changing different set of handlebars. There will be no need for the users to purchase multiple separate exercise systems, for example one for exercising lower limb muscles, another for exercising back muscles etc.

The proposed Isokinetic multifunctional hydraulic system besides being useful for rehabilitating the users having injuries can also be used by athletes/sport persons to train themselves or by a coach where an athlete/sport person's muscular resistance is required to be met with a proportional amount of resistance throughout a range of motion. Further, the proposed Isokinetic exercising system may be set to offer concentric-concentric resistance.

Embodiments of the present invention present an Isokinetic exercise and rehabilitation system. The system includes a base, a pedestal configured on the base, a vertical member attached to the base, and a vertical column slidably disposed within the pedestal. The vertical column including a pivot plate mounted thereon, wherein the vertical column is height adjustable relative to the pedestal. The system further includes a bracket pivotally mounted on the pivot plate, the bracket is adapted for resting a rotary actuator, the rotary actuator is positionable at a first position parallel along an X-axis of the base and a second position parallel along a Y-axis of the base to enable a user to connect a selected exercising attachment to a torque arm connected a central shaft of the rotary actuator to perform an intended exercise. The system further includes a resistance control valve unit connected to the rotary actuator through an intake manifold, the resistance control unit comprising a pair of rotatable dials adapted for use by the user performing the intended exercise to rotatably set a range of resistances selectively for opposing movements i.e. flexions and extensions in order to accommodate varying exerted forces by the user performing the intended exercise.

The system further includes an electronics module housing one or more angle sensors, and one or more pressure sensors configured to detect rotational angle and pressure related data in form of voltages associated with the rotary actuator, the electronics module is further configured to relay the detected voltages to an A to D converter to convert the detected voltages in a digital form, which is then relayed to a display unit by the A to D converter. The display unit is configured to embody a program product for receiving, and processing the detected voltages in the digital form from the A to D converter to at least: generate and display a muscular performance assessment report in real-time, store the received voltages or the muscular performance assessment report for future comparison, enable printing the muscular performance assessment report, and allow the user to configure a next intended exercise.

These and other features, advantages and objectives of the invention will become apparent from the detailed description below, in light of the accompanying drawings.

BRIEF DESCRIPTION OF THE ACCOMPANYING DRAWINGS

The present invention is illustratively shown and described with reference to the accompanying drawings, in which.

DESCRIPTION OF THE PREFERRED EMBODIMENTS

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

As discussed above, the prior art Isokinetic machines are more complex, and bulky and normally only a skilled user is able to operate such machines and can tutor on how to do any muscular performance measurements and tests using such machines. In order to overcome these shortcomings, the inventor herein has designed a less complicated, and portable multifunctional Isokinetic exercise system using which a user can do the exercises on his own without requiring formal skills to operate or use the system. Further, the system is computerized or connected to a computer such that the users can visually see their muscular performance while doing the exercises and if required keep on loading or unloading the resistance values during concentric and eccentric movements. The proposed Isokinetic exerciser machine uses specialized components for strength training and performance measurement. The proposed exercising system is able to control the speed of movement eliminating momentum. Thus, the proposed system can be realized as safer than using free-weights along and can be considered as an ideal machine for rehab purpose. Using the proposed machine, one can control amount of force user exerts, lowering risk of any injury. Further, the system is able to generate one or more muscular performance reports, showcasing the strength, endurance, comparison of range of motion in both strength values and power values.

The proposed multifunctional computerized Isokinetic exercise system and method of using the system will now be discussed in detail with respect to the accompanying drawings, particularly FIGS. 1-15, wherein like numerals designate identical or corresponding parts throughout the several views.

Figure 1:
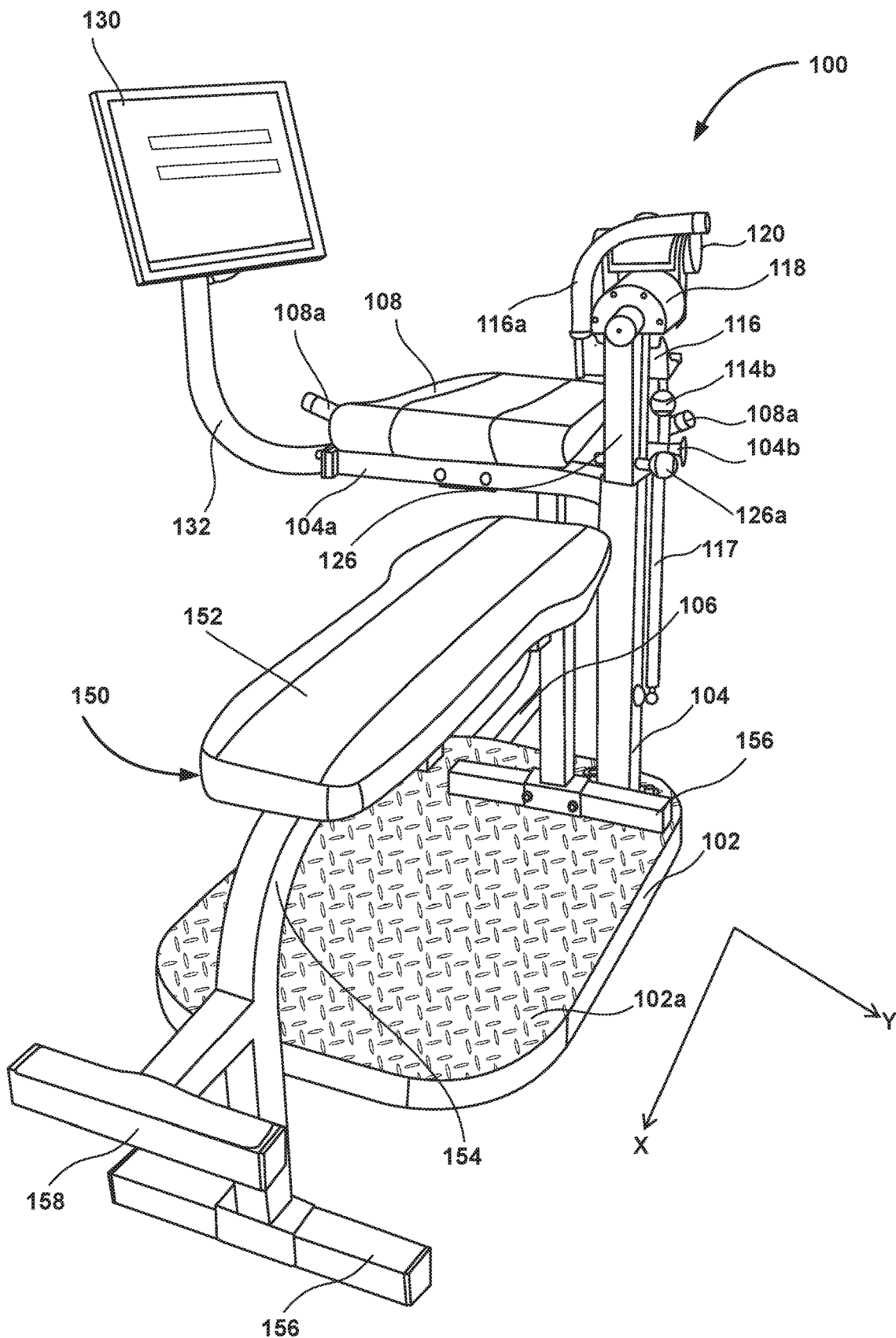
FIG. 1 shows a perspective view of a multifunctional Isokinetic exercise system configured under one setting, according to an embodiment of the present invention.
Figure 2:
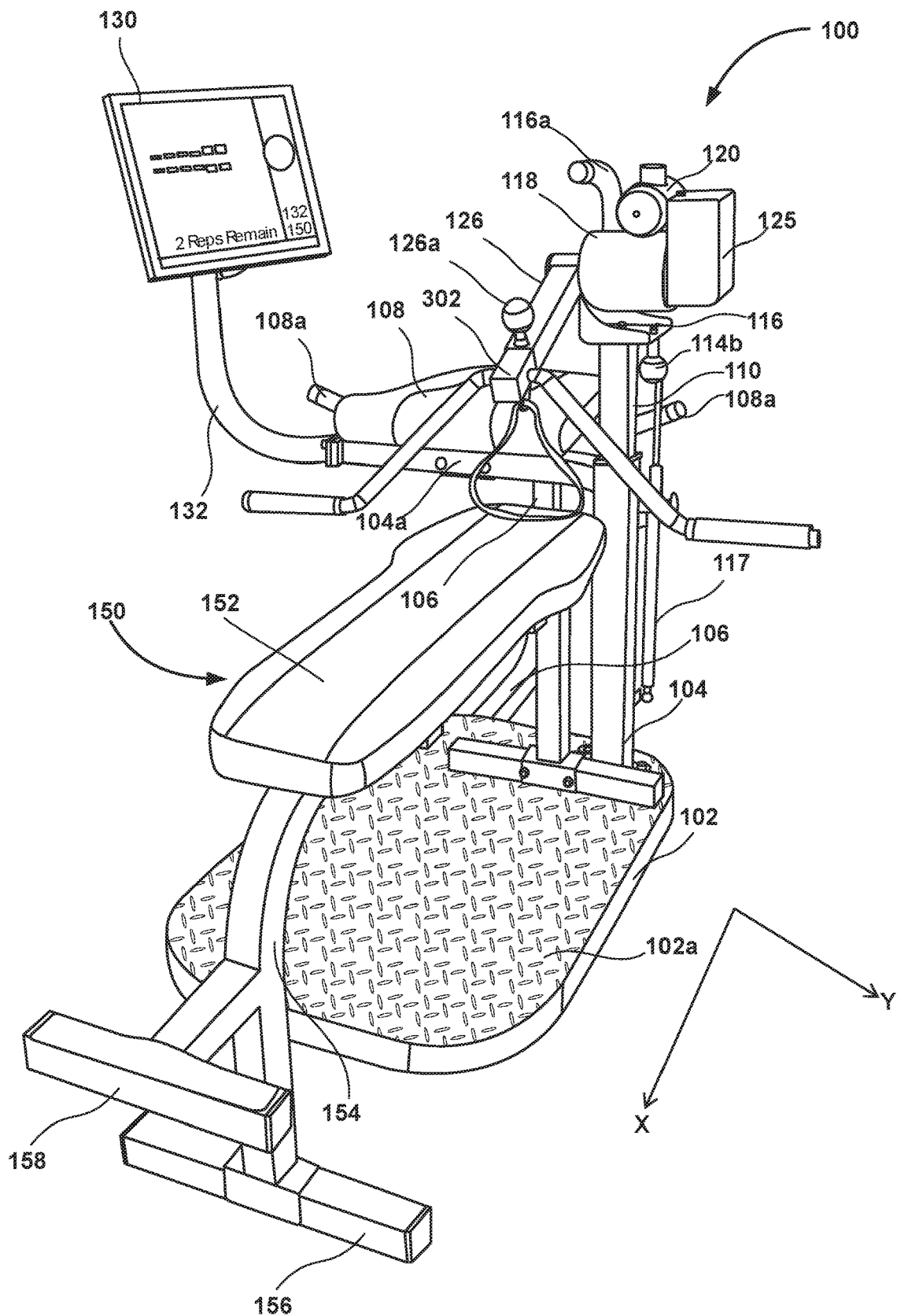
FIG. 2 shows a perspective view of the Isokinetic exercise system of FIG. 1 configured under another setting, according to an embodiment of the present invention.

Referring to FIGS. 1-15, particularly to FIGS. 1-2, the Isokinetic exercise system or machine of the present invention is shown as 100. The exercise system 100 includes a horizontal base 102. The base 102 comprises a piece of substantially rigid material having a bottom surface which allows the base 102 to be placed flat on a floor. The base 102 is somewhat rectangular in shape, but one should understand various shapes and sizes for the base 102 are possible such as for example oval, polygonal, just one should ensure the design of the base 102 provides a stability while withstanding the weight of the machine components mounted onto it and the weight of person/user exercising over the base 102. The base 102 according to the embodiment is sized as 65 cms wide×90 cms long.

The base 102 includes an upper surface 102a having a support area for mounting a hollow pedestal or stand 104 thereon. The pedestal 104 is preferably made of rigid material such as metals. In the example embodiment shown in FIG. 1, the pedestal 104 is removably mounted over the base 102 using suitable fasteners such as nuts and bolts. In another embodiment, the pedestal 104 and base 102 may be configured as a unitary product or the pedestal 104 may be fixedly attached onto the base 102. In an example, the pedestal 104 is square shaped with dimension 65 mm×65 mm×2.5 mm. However, it should be understood that the pedestal 104 may be constructed in different shapes and dimensions.

Figure 7:
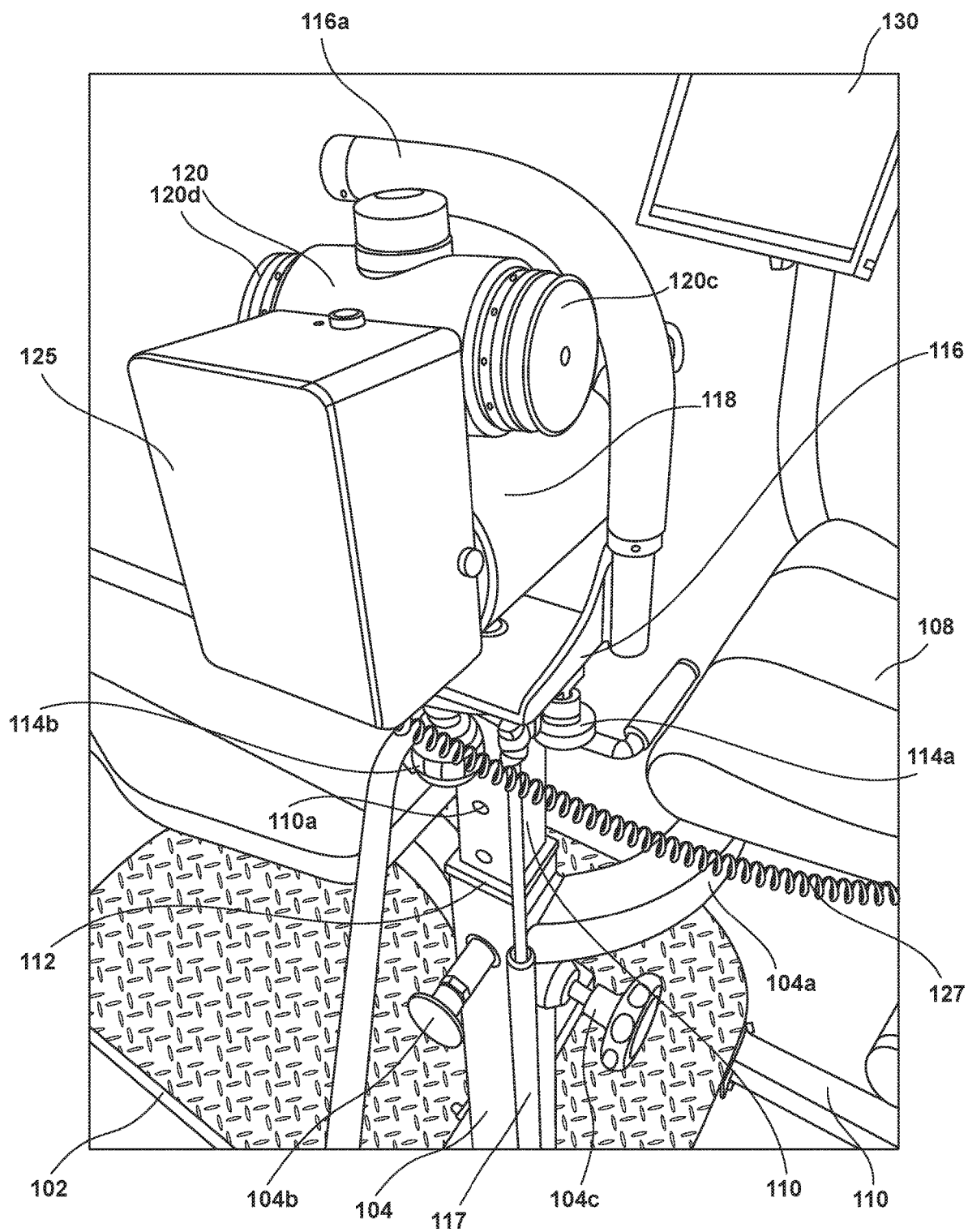

The pedestal 104 according to the embodiment further includes a curved extension or an L-type bend 104a fixedly attached and extending away from the pedestal 104 substantially parallel to the base 102. In some other embodiment, the curved extension 104a may be removably attached to the pedestal 104 using suitable fasters. The curved extension 104a may be square, rectangular, or configured in many different shapes. The pedestal 104 may further include a spring loaded pop pin 104b and a pressure disc knob 104c as best seen in FIG. 7. In the example shown in FIG. 1, the support area on the base 102 is seen located substantially at one of the side corners of the base 102, however, one should understand the support area can be located at other locations over the upper surface 102a of the base 102.

Figure 14:
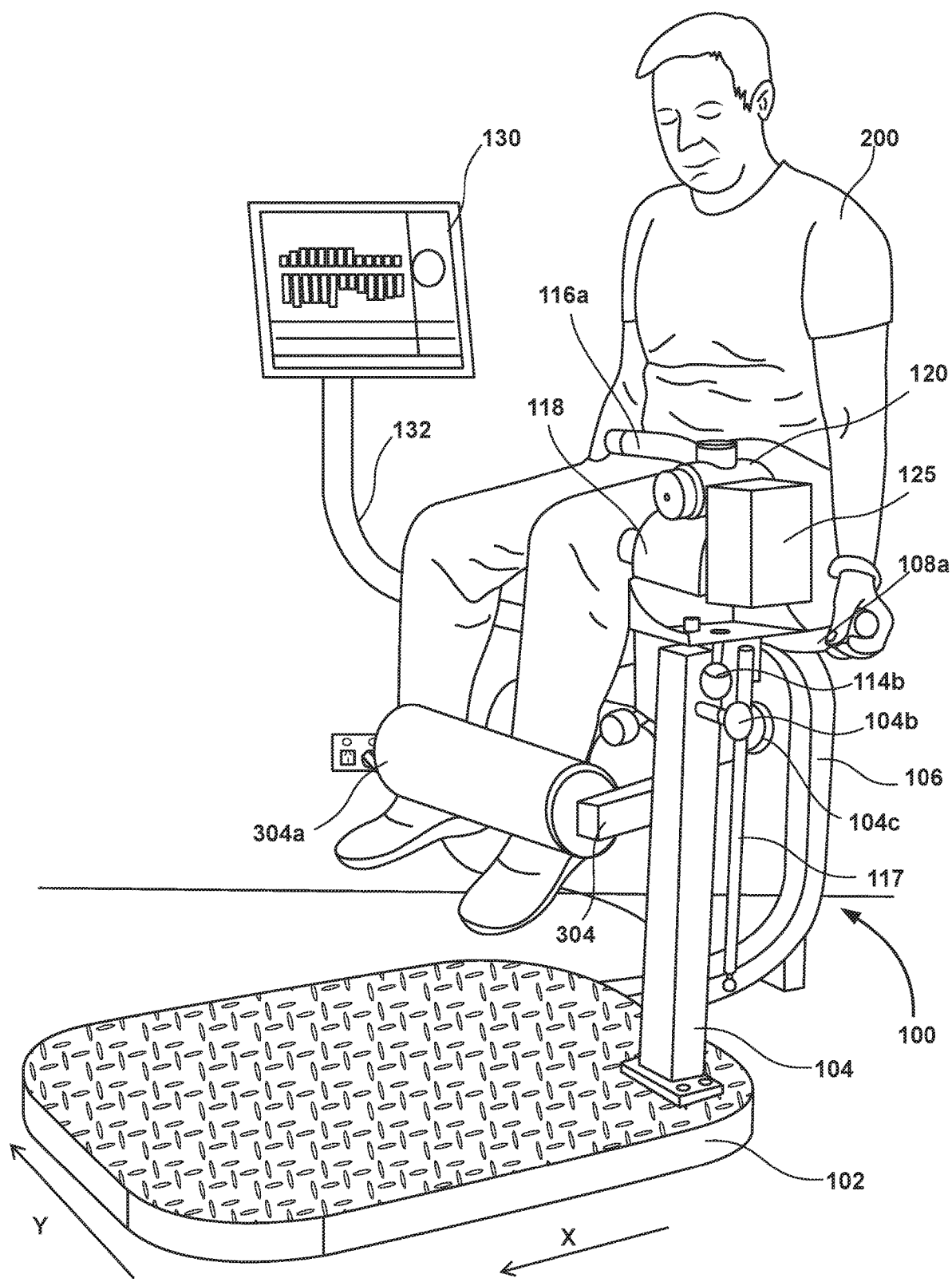
Figure 15:
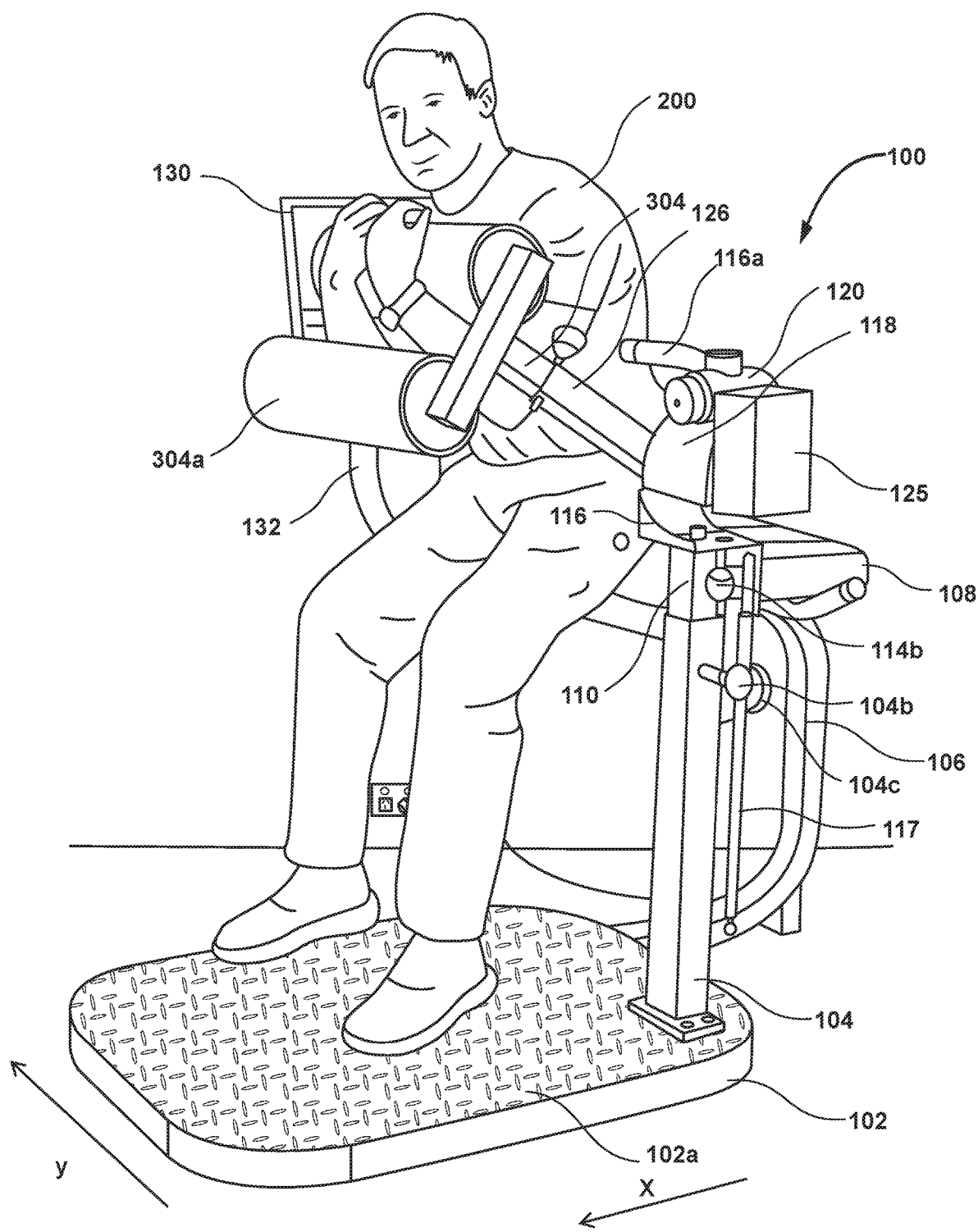

According to the embodiment, the exercise system 100 further includes a vertical member 106 removably attached to the base 102 using suitable fasteners such as nuts and bolts. The vertical member 106 is preferably made of metallic material such as stainless steel. In some other embodiment, the vertical member 106 may be fixedly attached to the base 102 making them a unitary product. The vertical member 106 and the curved extension 104a of the pedestal 104 are used for mounting a seat 108 with side handles 108a. The seat 108 is rested over the vertical member 106 and the curved extension 104a of the pedestal 104 may generally be used for lower body conditioning such as for performing leg extensions and leg curls while seated as shown in FIG. 14. The seat 108 may also be used for performing other suitable exercises as well such as trunk related exercise as shown in FIG. 15. The handles 108a can be used by the user to stabilize while being seated.

In some other embodiments, the base 102, the pedestal 104 and the vertical member 106 can be constructed as a single unitary product instead of three piece configuration removably attached to one another.

Figure 12:
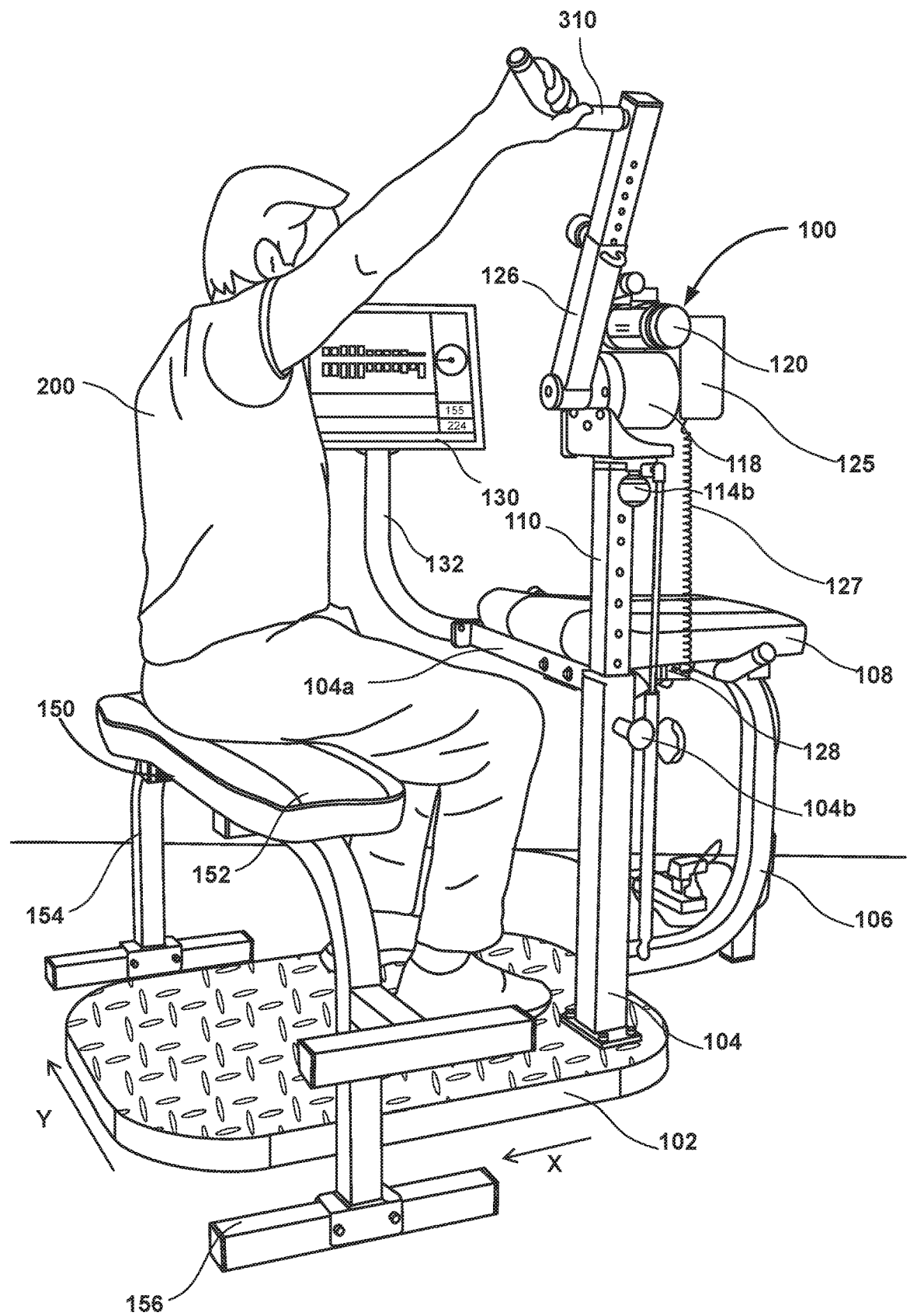

The system 100 also employs a positionable bench 150 as shown in FIG. 1-2, 12-13. The bench 150 comprises a elongated seat 152 that may be used by the user for performing seated exercises such as for example shoulder/chest press (FIG. 13), and single arm shoulder exercise such as shoulder abduction as shown in FIG. 12. The elongated seat 152 may also be used for laying over it with his or her back portion to perform certain exercises such as for performing shoulder press. The elongated seat 152 of the bench 150 may be supported by a vertical member 154. In one embodiment, the vertical member 154 may be a single piece product (say in substantially U shape). In other embodiment, there could be two vertical members spaced apart from each other and with a height that would be suitable for uses. The feet 156 of the vertical member 154 may be made flat and elongated to occupy larger surface area on rested surface to provide higher stability. Further, optionally, the vertical member 154 may further have a T shaped member 158 attached thereto. This T shaped member 158 may be used for holding or hanging certain exercise related attachments/handlebars. The bench 150 may be configured in variety of sizes, for example, in one embodiment it may be 1.2 mt in length×30 cms in width×50 cms in height.

Figure 11:
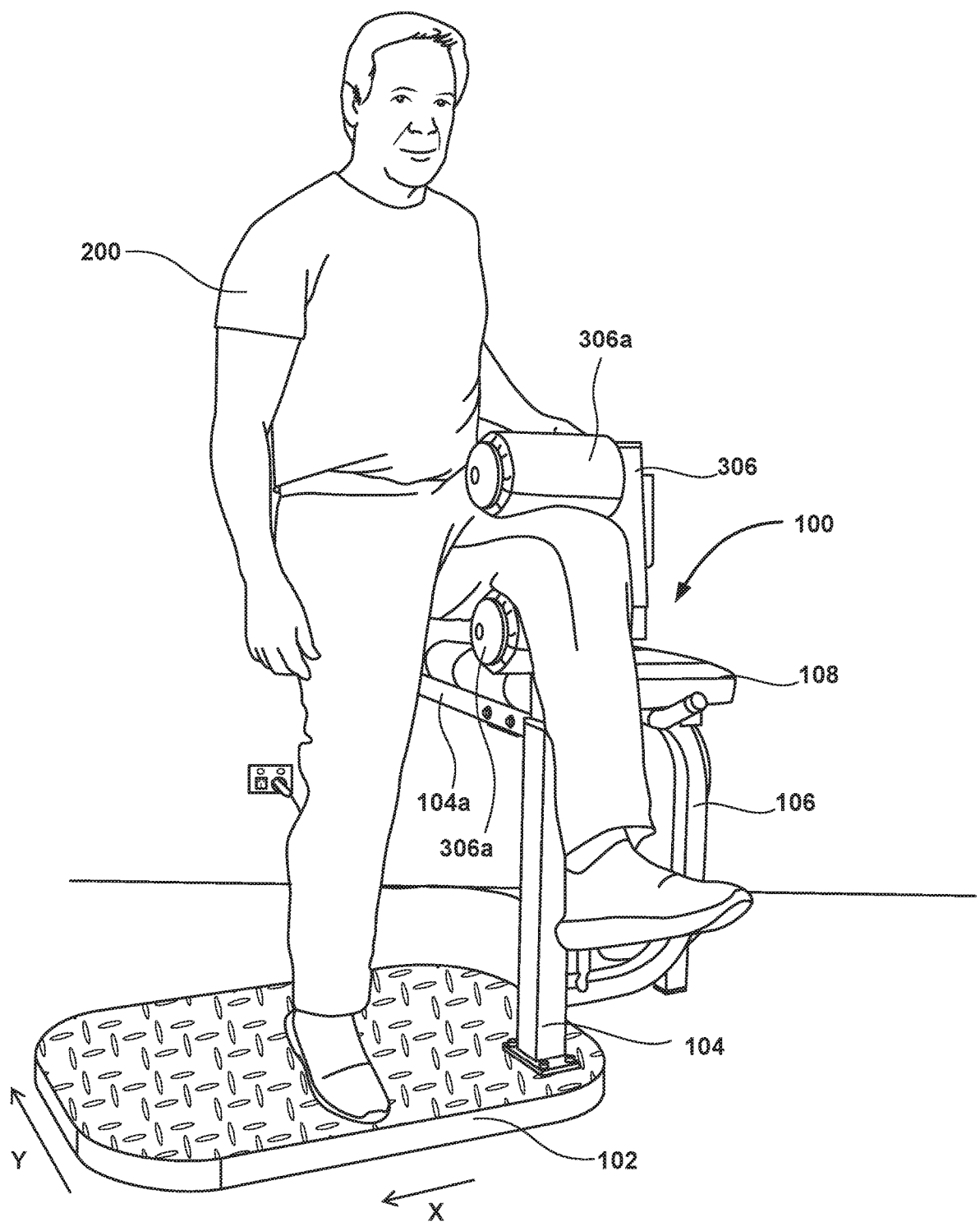
FIGS. 11-15 show some exemplary body exercises that can be performed utilizing the novel multifunctional Isokinetic exercise system of the present invention.
Figure 13:
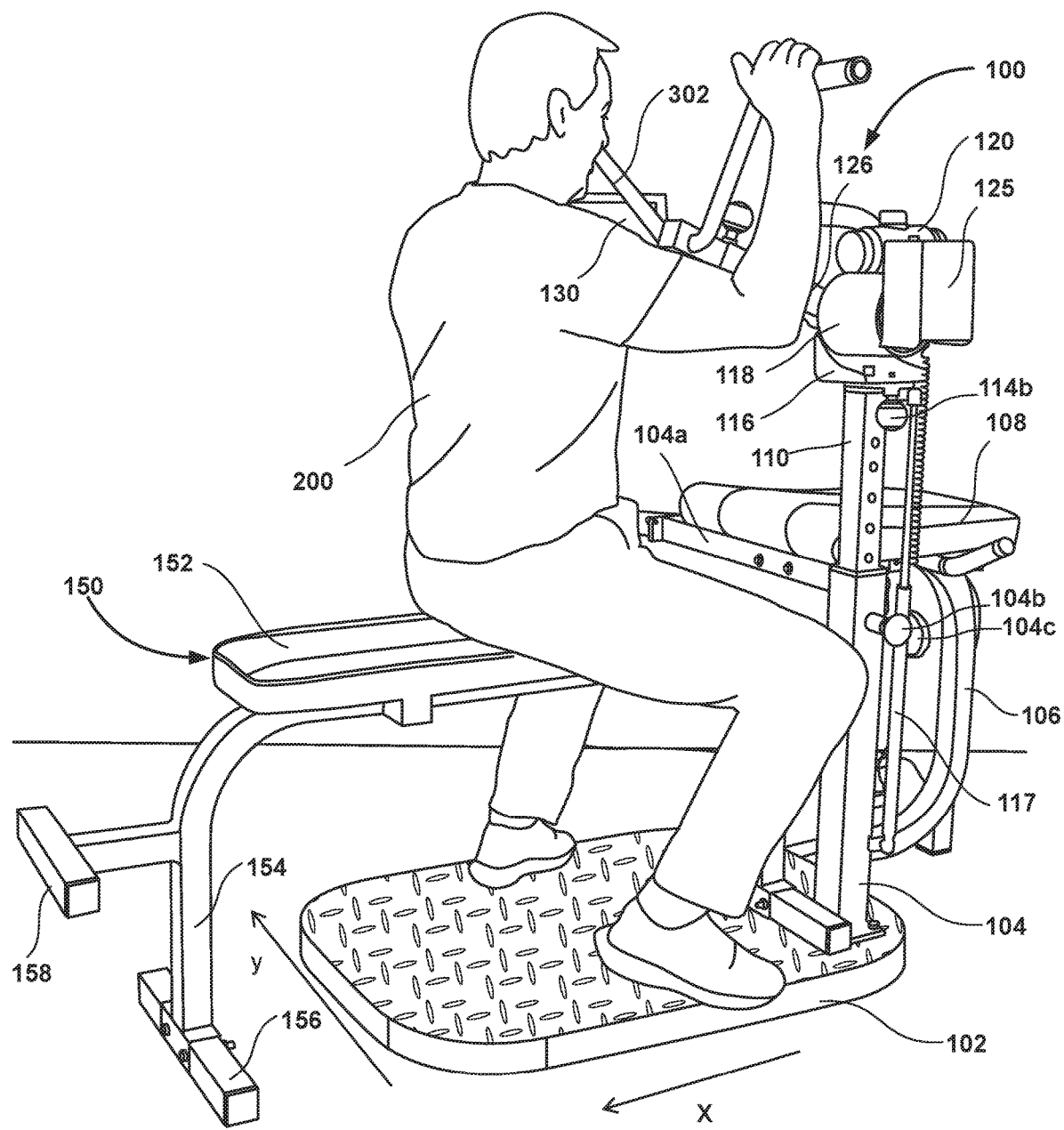

The bench 150 can be used with the proposed machine for performing various exercises such as shoulder abduction, shoulder press, bench press and so on. For performing certain exercises that can be done using the bench 150, the bench 150 may be placed either along X-axis of the base 102 (partly over the base 102) such as for doing shoulder press/chest press as shown in FIG. 13. Further, for performing exercise such as shoulder abduction as shown in FIG. 12, the bench 150 may be placed across the base 102 along the Y-axis of the base 102. Likewise, different exercises may be done by changing position of the bench 150 in relation to the machine or the base 102. Further, for performing some exercises, the bench 150 may be removed such as for example while doing hip exercise as shown in FIG. 11, one may not require the bench 150 and can be removed.

Figure 5:
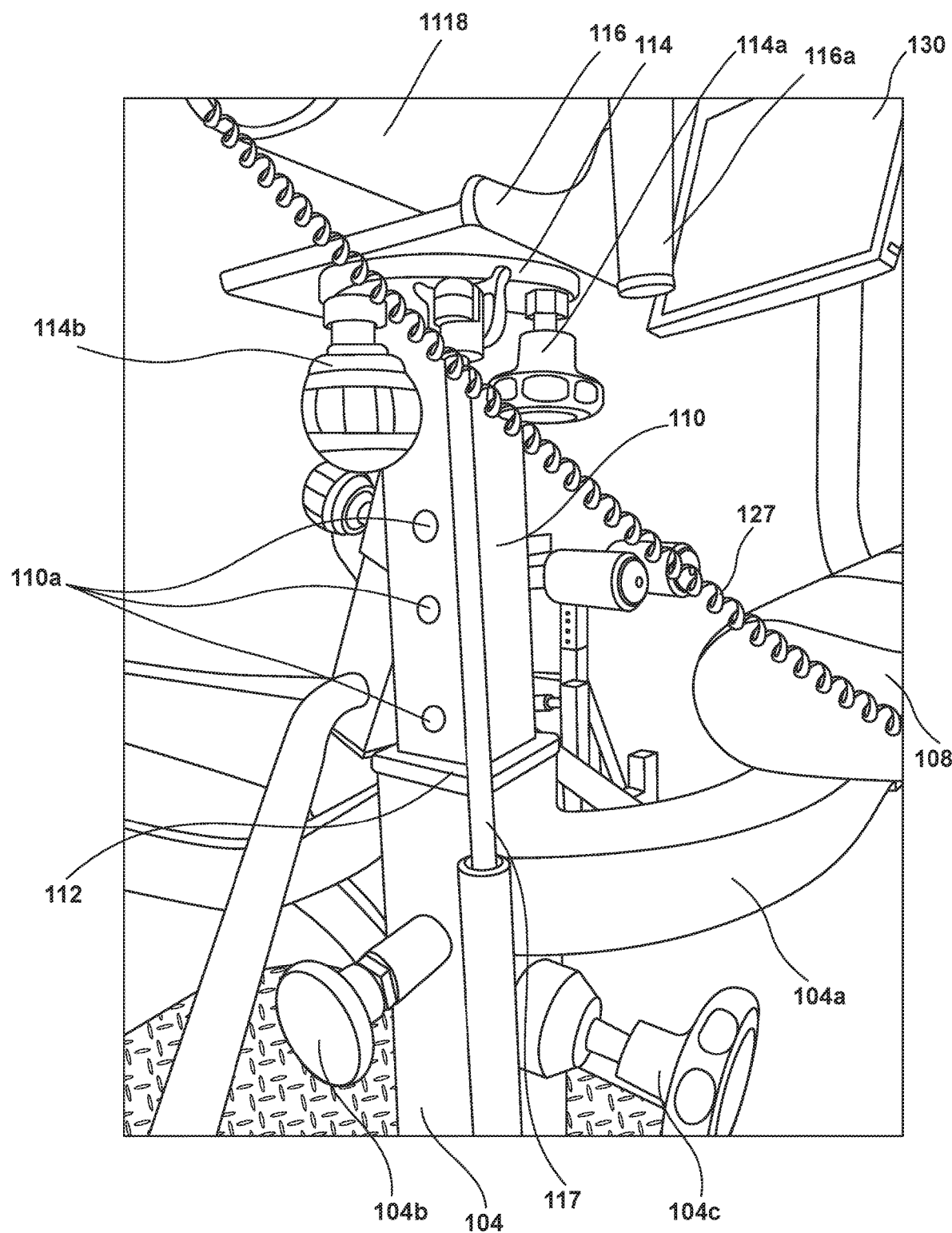
FIGS. 5-7 are perspective views of a portion of the Isokinetic exercise system of FIG. 1 or FIG. 2.

As seen in FIGS. 2, 5 and 7, the exercise system 100 includes a vertical column 110 slidably disposed within the hollow pedestal 104. In an example, the vertical column 110 is square shaped with dimension 50 mm×50 mm×3 mm. However, it should be understood that the vertical column 110 may be constructed in different shapes and dimensions. The vertical column 110 comprises a plurality of apertures or slots 110a located at one side. The vertical column 110 can be slidably vertically extended from the pedestal 104, and slidably retracted into the pedestal 104 to different heightened positions. To achieve a desired heightened position, one can operate the spring loaded pop pin 104b disposed on one side of the pedestal 104. In operation, the user can pull out the spring loaded pop pin 104b then pull or push down the vertical column 110 relative to the pedestal 104 and then release the spring loaded pop pin 104b so that the pin gets threaded into a selected aperture of the plurality of apertures 110a. Further, according to the embodiment, in order to provide a smooth slidable fitting between height adjustable vertical column 110 and the pedestal 104, an insert or sleeve 112 is disposed within the pedestal 104. The insert 112 is preferably made of nylon or like material and is laid between outer surface of the vertical column 110 (particularly the outer surface of the portion of the vertical column 110 within the pedestal 104) and the interior surface of the pedestal 104. In order to lock the height adjustable vertical column 110 in position relative to the pedestal 104, one can operate the pressure disc knob 104c. This increases safety and reliability of the system 100 ensuring the column 110 don't accidentally slide down injuring the user using the system 100.

According to the embodiment, the vertical column 110 includes a pivot plate 114 mounted on its top as shown in FIG. 5. As seen in FIG. 5, the pivot plate 114 further includes a locking knob 114a, and a spring loaded locking knob 114b. A bracket 116 is further removably mounted on top of the pivot plate 114. The bracket 116 is pivotally mounted at the center of the pivot plate 114. The locking knob 114a and the spring loaded locking knob 114b are operably configured to lock or securely hold the bracket 116 in its intended position. The bracket 116 further includes a stabilizing handle 116a attached thereto. The stabilizing handle 116a may be used for performing certain exercises or used to push or pull the vertical column 110 during height adjustment against a gas strut 117. In operation, a user can turn the locking knob 114a to release its connections to the bracket 116, and pull or open the spring loaded locking knob 114b to release or loosen its connection to the bracket 116, once the connection or grip of these knobs 114a, 114b are released, the user is able to rotate the bracket 116 at its pivotal point to desired orientation or position.

According to the embodiment, as seen in FIGS. 1, 2 and 5, the exercise system 100 further includes the gas strut 117. The gas strut 117 may be adjustable gas strut in which different internal pressures can be set using an Allen key to withstand varying pressure exerted by the load over the plate 114. Alternatively, the gas strut 117 may be chosen that is preset to specific pressure that may be suitable to use for the presented invention. The gas strut 117 is connected at its one ball mount to the pivot plate 114 and to the pedestal using its other ball mount. The gas strut 117 operates to extend or retract against the load pressure and supports up or down adjusted movement and repositioning of the vertical column 110. The gas strut 117 ensures any accidental sliding down of the vertical column 110. The internal operational mechanism of the gas strut 117 is intentionally omitted herein. In other embodiment, one can even use some alternative mechanism such as spring mechanism to ensure a controlled movement of the vertical column 110 relative to the pedestal 104.

Figure 6:
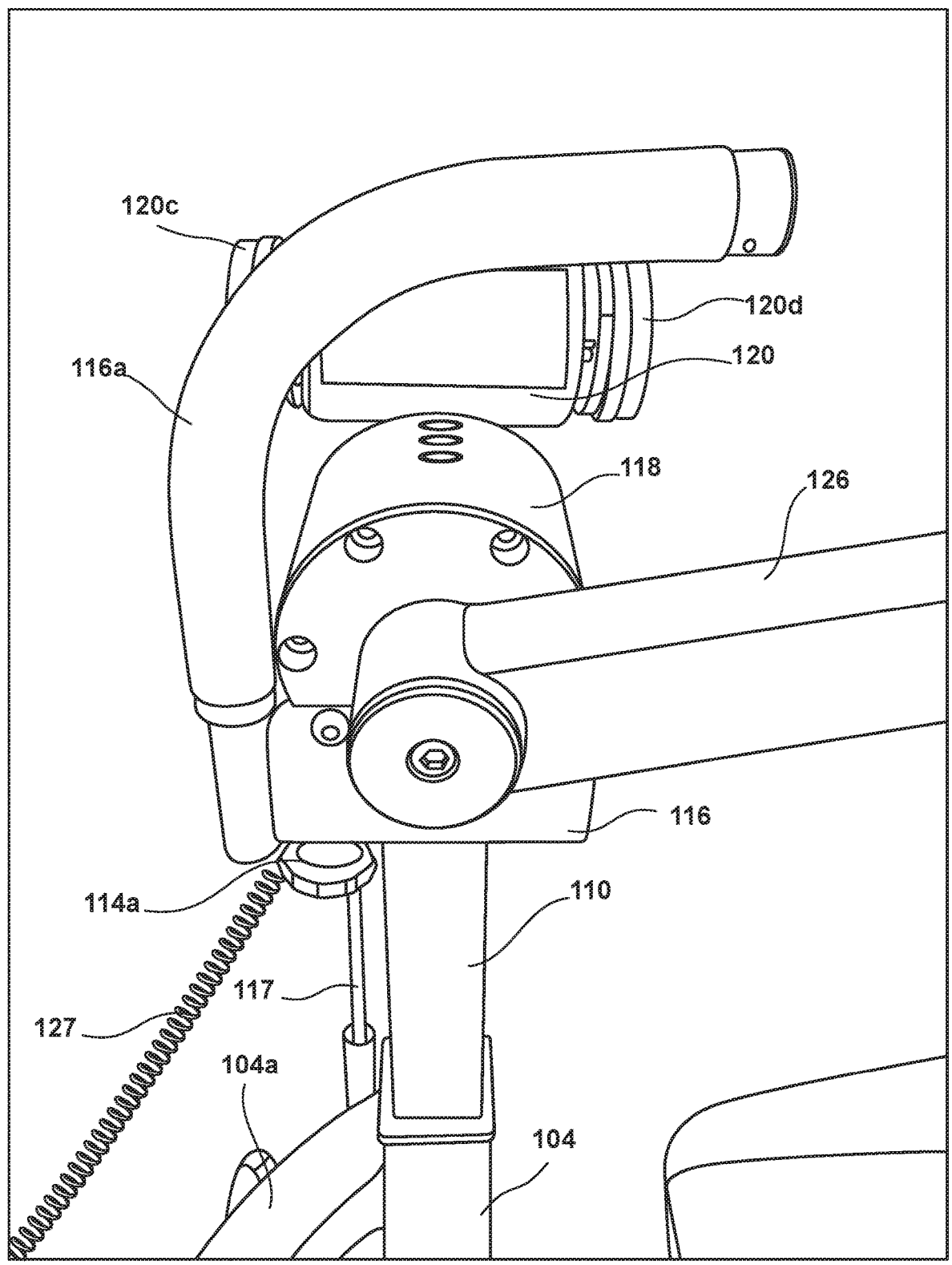

According to the embodiment, as seen in FIGS. 2, 6 and 7, the bracket 116 (mounted on the pivot plate 114) is adapted for resting a rotary actuator 118. According to the embodiment, the rotary actuator 118 is a vane-type rotary actuator or pump. The vane-type rotary pump 118 is selected for this application because oil or liquid can be discharged by this type of pump 118 at high pressure and the pump 118 of this type is very compact for uses. Further, irrespective of the increase in pressure, the amount of discharged oil (or rate of liquid flow) remains constant. In operation, the moving vane configured inside the pump 118 carries oil along with it from an input port to an output port of the pump 118. Since the proposed hydraulic exercise system 100 is intended to develop lager amount of force, the use of vane type rotary pump 118 is an ideal choice. Further, depending upon the direction of oil flow through the pump 118, a centrally located shaft/actuator (not seen) therein can rotate clockwise or anticlockwise with rotation of the vane. According to the embodiment, the rotation can be up to 270 degrees in clockwise or anticlockwise direction.

Figure 3:
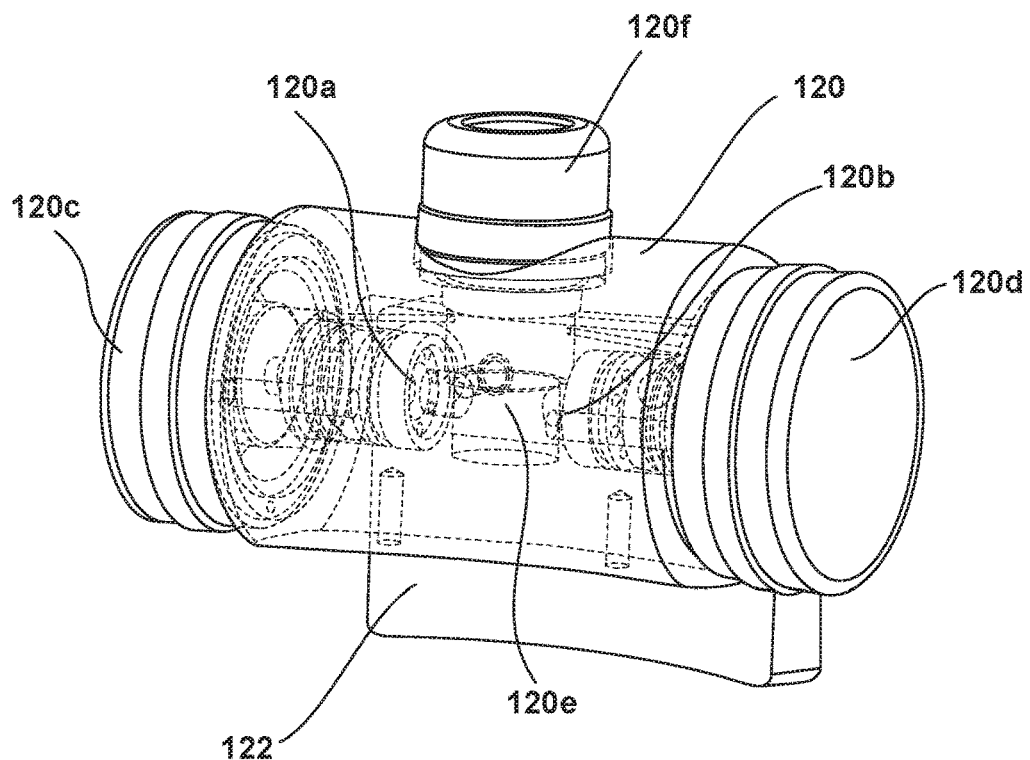
FIG. 3 shows a front perspective view, particularly an internal view of a resistance control valve unit with an intake manifold connected thereto, according to an exemplary embodiment of the present invention.
Figure 4:
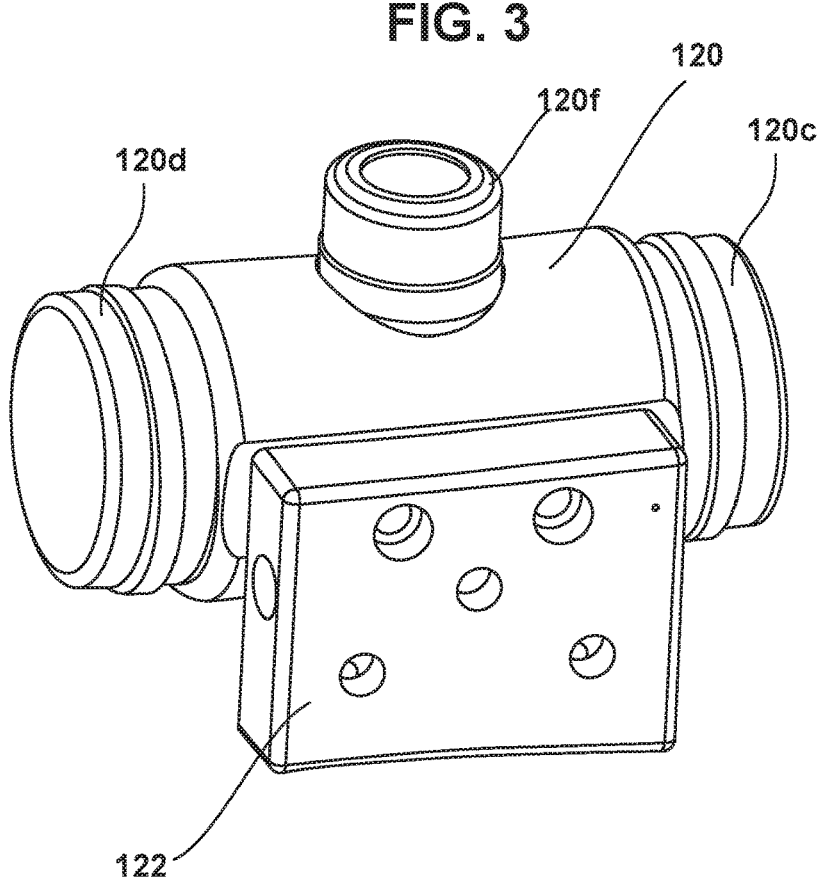
FIG. 4 shows a back perspective view of the a resistance control valve unit with the intake manifold connected thereto.

Further, the outlet port of the pump 118 is connected to a resistance control valve unit 120 through an intake manifold 122 (as shown in FIGS. 3, 4 and 7). The intake manifold 122 functions to receive the discharged oil from the pump 118 and divert the oil horizontally through the resistance control valve unit 120 from left hand side to right hand side and vice versa. In other words, the intake manifold 122 directs the received oil from the pump 118 to a left hand aperture 120a then to a central chamber 120e and then out from a right hand aperture 120b of the control valve unit 120 and vice versa. The resistance control valve unit 120 further includes a left hand side rotatable dial 120c and a right hand side rotatable dial 120d designated to independently control extension and flexion movements of a body part being exercised or simulated. The two dials 120c and 120d are selectively rotatable by the user to select a resistance on a scale of 1-10. The selection of particular resistance value from the two dials 120c, 120d ensures the degree to which the corresponding apertures 120a, 120b will open up for allowing flow of oil therethrough. The two dials 120c, 120d facilitate independent resistance control to accommodate varying exerted forces by the user during exercises. The resistance control allows to independently set resistance for flexions and extensions, for example, a user performing knee extension or flexion exercise using the proposed system 100 (or using the two dials 120c, 120d) can set different resistances for opposing movements i.e. flexion and extension of the knee, if the user sets higher resistance for knee extension then the system 100 won't let the user push even if the user applies greater force (e.g. using designated exercising attachment/handlebar) and keep the speed constant. Applying greater force in either direction will internally obstruct the flow of oil across the central chamber 120e of the resistance control valve unit 120 and the oil will accumulate and try to push against a spring loaded cap 120f trying to expand and escape therefrom.

Further, as seen in FIGS. 1-2, and 6, a torque arm 126 is connected to the shaft of the pump 118 so as to rotate with the rotation of the shaft. The exercising user connects a selected exercising attachment to the torque arm 126 and positions/locks it in place using a spring loaded locking knob 126a provided on the torque arm 126. According to the embodiment, the torque arm 126 may be positioned parallel to X-axis of the base 102 as shown in FIG. 2, or the torque arm 126 may be positioned parallel to Y-Axis of the base 102 as shown in FIG. 1. The ability of the system 100 to facilitate rotation of the pump's position 118 by 90 degrees makes it possible to use the torque arm 126 under two different positions/settings. The possibility for pivotal rotation of the bracket 116 as described above enables rotation of the pump 118 (since the pump 118 is directly mounted over the bracket 116) and this provides two different settings for the motor's shaft to connect to the torque arm 126.

Depending upon the type of setting or configuration chosen, different exercise attachments/handlebars may be used. As shown in the FIG. 10, the different exercise attachments 302-310 may be of nature as shown. The different exercise attachments 302-310 may be used for different exercises. For example, the attachment 302 may be used for chest/shoulder press as also shown in FIG. 13. The attachment 304 with two pads 304a may be used for performing seated trunk exercise (as shown in FIG. 15) or seated exercise related to knees (as shown in FIG. 14). For using this type of attachment 304, the user can place the legs or hands under the pads 304a for comfort. Further the exercise attachment 306 with two pads 306a (very similar to attachment 304, but smaller in dimension), the user may use it for performing hip exercise (as shown in FIG. 11). The attachments 308 and 310 (single bar one being smaller and one larger) may be used for performing shoulder abduction or shoulder extensions. The exercises described above that can be performed using different exercise attachments 302-310 are merely exemplary and there can be other exercises related to trunk musculature, extremities, back, neck, back, chest, legs, arms and so on that can be performed by selectively using attachments 302-310.

Figure 9:
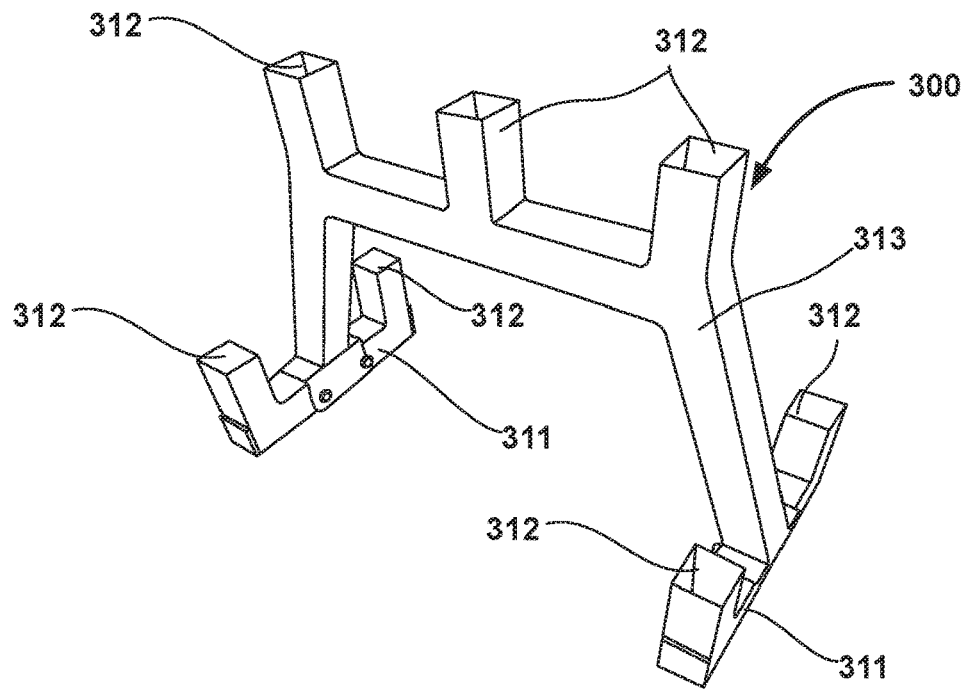
FIG. 9 shows a stand arrangement for removably mounting multiple exercise attachments that can selectively be used while working on the Isokinetic exercise system of FIG. 1.
Figure 10:
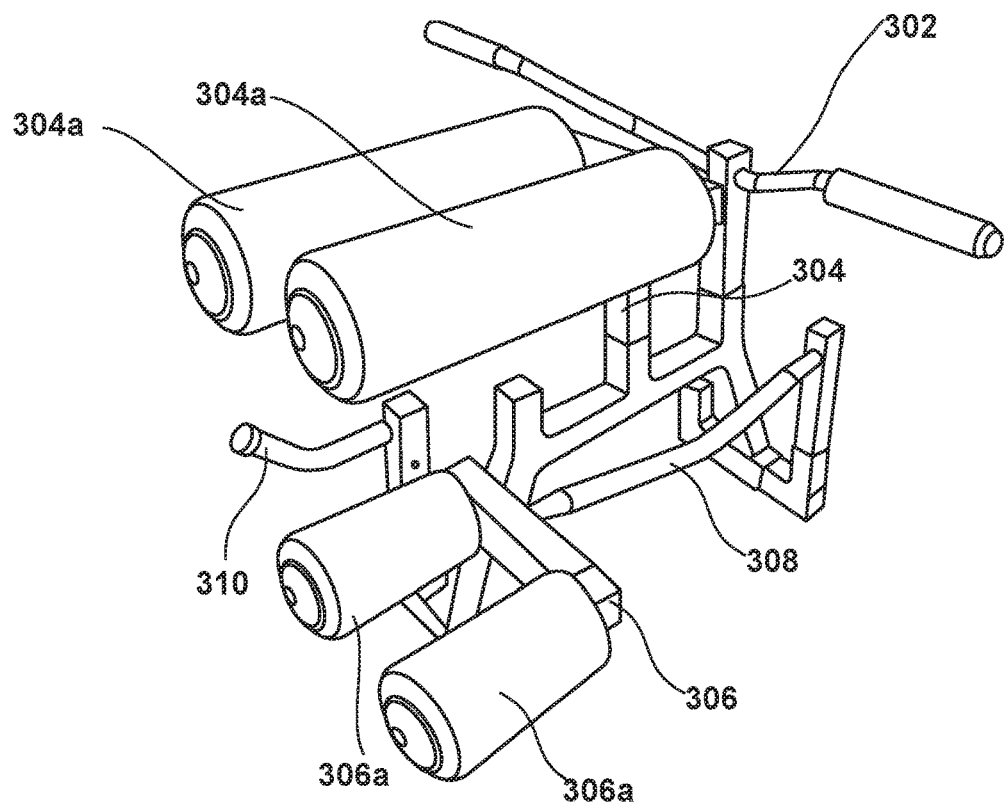
FIG. 10 shows the stand arrangement of FIG. 9 with the different exercise attachments mounted thereon.

Further, the present invention also discloses a specialized stand 300 (as shown in FIG. 9) configured for mounting the exercising attachments 302-310 (as shown in FIG. 10), according to an exemplary embodiment. The stand 300 comprises a pair of base supports 311, and a vertical mount 313 coupled to the pair of base supports 311. Each vertical mount 313 and each of the base support 311 comprises one or more connecting limbs 312 that removably engaged to engaging ends provided in each of the exercise attachments 302-310. Although, five exercise attachments 302-310 are shown mounted on the stand 300. It should be understood one can customize the stand 300 for holding more or less numbers of exercise attachments.

Further, as seen in FIGS. 2 and 7, the exercise system 100 includes an electronics module configured in the form of a box/case 125. The intake manifold 122 attached to the resistance control unit 120 may also be integrated with the electronics module 125 as a single unit. The electronics module 125 houses one or more angle sensors, and one or more pressure sensors configured to detect the rotational angle of the shaft of the pump 118 and pressure developed due to flowing oil within the pump 118, respectively. The module 125 further houses a circuitry for driving the angle and pressure sensors. The circuitry may include one or more microcontrollers, memory and other electronic components. The one or more microcontrollers may operate on embedded logics for receiving, and processing the detected angular and pressure related data from the sensors. The term "embedded logics" used herein is used in broader sense that include programs, or routines, or interfaces stored in the memory that the microcontrollers can fetch and execute to perform the function of receiving and processing of the detected angular and pressure related data (in the form of voltage). The detected voltage signals (or the angular and pressure data) is then relayed to a custom made A to D converter 128 (seen in FIG. 12), by the electronics module 125. In the example shown, the A to D converter 128 is positioned underneath the seat 108. The A to D converter 128 transform the analog form of voltage to digital form and is then feed to a display unit 130 for display and storage. For relaying data or communicating data, a wired connection (such as wiring 127) may be used from the electronics module 125 to A to D converter 128. Further, another wired connection may be used to relay generated information/data from A to D converter 128 to the display unit 130. In some other embodiment, a wireless connection may be used for relaying data/information from the electronics module 125 to the A to D converter 128, and from the A to D converter 128 to the display unit 130.

Figure 8:
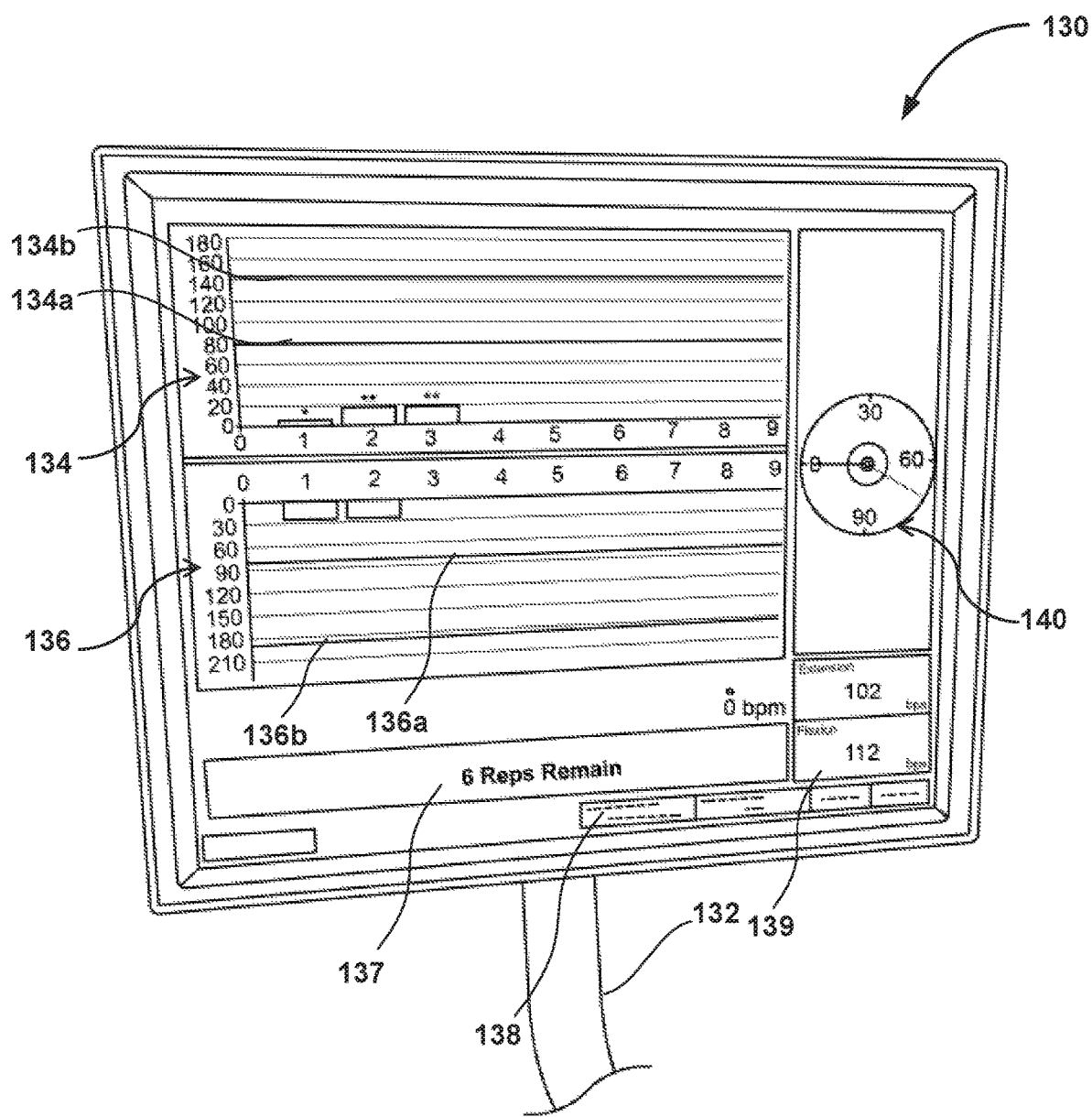
FIG. 8 shows a display unit adapted for displaying user's muscular performance in real time while performing an Isokinetic exercise using the Isokinetic exercise system of FIG. 1.

The display unit 130 may be communicatively linked to a storage unit for storage of the data received from the A to D converter 128. The display unit 130 according to the example embodiment (as shown in FIGS. 1 and 2) may be connected to the curved extension 104a of the pedestal 104 using a connecting arm 132. The display unit 130 may be configured in the form of a touch screen display panel so as to allow the user to navigate through user interfaces by simple touch of his or her fingers. In some other embodiment, the display unit 130 may be configured in the form of a non touch screen with a keypad for inputting the selection. According to the embodiment, the display unit 130 embodies a program product to receive the data from the A to D converter 128 and display the same in different graphical forms such as for example but not limited to a bar graph (as shown in FIG. 8), and/or a pie charts. Also, the display unit 130 can display heart rate using transmitter and receiver displayed on the screen.

Using the program product configured on the display unit 130, the user can for example set an exercise that he or she wants to perform using the system 100, and next, the user can configure number of reps for each set of exercise, and then begin the exercise. While performing the intended exercise, the display unit 130 will display the muscular performance of the user in real-time and facilitate the user with printing the performance report. The performance report or data can also be stored by the display unit 130 for future retrieval or comparison with future muscular performances of the user to make an assessment on how helpful the exercise has been in recovery or rehabilitation process. Further, based on the report generated or live display of the muscular performance, the user can take appropriate decisions and update his or her exercise patterns or exercise sets for quick recovery. The stored performance data can also be shared (using some communication medium such as internet), by the display unit 130 with remote healthcare facilities or like facilities for any advises or necessary guidance.

Assuming a user sets a hip extension and flexion exercise with a set of 9 reps, FIG. 8 shows an exemplary display interface (or a user interface) that may be displayed to the user performing muscular extensions and flexions for hip. As seen, the display unit 130 will display a bar graph generated in real time for each rep representing forward movement and backward movement (two way muscular movements). A bar graph 134 (Reps Vs torque) may represent hip extension related data, and a bar graph 136 (Reps Vs torque) may represent hip flexion related data in real time. The graphs will also display a threshold torque value (134a for extensions and 136a for flexions) and a maximum value achieved during muscular extension and flexions (represented by 134b and 136b). The interface may also show, number of reps remaining 137 in the exercise set, and best performed hip extension and flexion values 138 (which is 134b/136b values (144 Nm/189 Nm) here). The interface may also allow the user to skip the rep, or cancel the exercise set, latest extension and flexion value 139. The clock representation 140 for rotational angle of the torque arm 126. The report as shown displayed in FIG. 8 over the display unit 130 is exemplary. The system 100 is configured to display reports in various forms, such as for example, report showing strength as a measure of time duration for reps and torque, report showing endurance in the form of bar chart and strength curve, and comparison of range of motion in both strength values and power values (as shown in FIG. 8).

FIGS. 11-15 shows different exemplary strength training exercises that can be performed using the proposed invention.

FIG. 11 in particular shows a user 200 performing hip exercise. As seen, the proposed system 100 is configured in its first configuration with the pump 118 laid parallel to the X axis of the base 102. The user 200 then connects the exercise attachment 306 to the torque arm (not seen). The user 200 then places his leg under the two pads 306a of the attachment 306, and make two way movement of hip (muscular extension and flexion), and while performing the exercise, the user 200 can vary resistance by operating the two resistance control dials of the resistance control unit. The user 200 will be able to independently control extension movement or flexion movement. No matter how hard he try to make the movements in either direction, due to applied resistance, the user exerted force will not allow him to hit harder and the speed will remain constant. In either direction he can load and unload the resistance anytime and continue to do the exercise and at the same time monitor his performance via the display unit (if that's powered ON). The display unit can be powered ON using standard power supply via power outlet, and once the display unit is ON, it will display the muscular performance of the user that can then be assessed for accommodating any suitable changes in the exercises to quicken the recovery process.

FIG. 12 in particular shows the user 200 performing shoulder abduction. As seen, the proposed system 100 is configured in its first configuration with the pump 118 laid parallel to the X axis of the base 102. The user 200 then connects the exercise attachment 310 to the torque arm 126. This exercise is preferably performed using the bench 150 with the user 200 seated on it. The user 200 can then grip the attachment 310 and perform the exercise. While performing exercise, the user 200 can vary resistance by operating the two resistance control dials of the resistance control unit 120. The user 200 will be able to independently control movement in either direction. No matter how hard the user 200 tries to make the movements in either direction, due to applied resistance, the user exerted force will not allow him to hit harder and the speed will remain constant. In either direction he can load and unload the resistance anytime and continue to do the exercise and at the same time monitor his performance using the display unit 130. The display unit 130 will display the muscular performance of the user that can then be assessed for accommodating any suitable changes in the exercises to quicken the recovery process.

Unlike the exercises shown in FIGS. 11-12, FIG. 13 in particular shows the user 200 performing shoulder/chest press exercise. As seen, proposed system 100 is configured in its second configuration with the pump 118 laid parallel to the Y axis of the base 102. The user 200 then connects the exercise attachment 302 to the torque arm 126. This exercise is preferably performed using the bench 150 with the user 200 seated on it. The user 200 can then grip the attachment 310 with two hands and perform the exercise. While performing exercise, the user 200 can vary resistance by operating the two resistance control dials of the resistance control unit 120. The user 200 will be able to independently control movement in either direction (extensions and flexions). No matter how hard the user 200 tries to make the movements in either direction, due to applied resistance, the user 200 exerted forces will not allow him to hit harder and the speed will remain constant. In either direction he can load and unload the resistance anytime and continue to do the exercise and at the same time monitor his performance using the display unit 130. The display unit 130 will display the muscular performance of the user that can then be assessed for accommodating any suitable changes in the exercises to quicken the recovery process.

FIG. 14 in particular shows the user 200 performing knee extensions and flexions. As seen, proposed system 100 is configured in its second configuration similar to FIG. 13. The user 200 then connects the exercise attachment 304 to the torque arm 126. This exercise is performed using the seat 108 and two handles 108a with the user 200 seated on it. The user 200 then places his leg under the pads 304a. Then holding the handles 108a perform his exercise. While performing exercise, the user 200 can vary resistance by operating the two resistance control dials of the resistance control unit 120. The user 200 will be able to independently control movement in either direction (extensions and flexions). No matter how hard the user 200 tries to make the movements in either direction, due to applied resistance, the user 200 exerted forces will not allow him to hit harder and the speed will remain constant. As desired, in either direction the user 200 can load and unload the resistance anytime and continue to do the exercise and at the same time monitor his performance using the display unit 130. The display unit 130 will display the muscular performance of the user that can then be assessed for accommodating any suitable changes in the exercises to quicken the recovery process.

FIG. 15 shows the user 200 performing trunk extensions and flexions using the same set-up of FIG. 14. The user 200, however this time around the user 200 places his arms under the pads 304a. While performing exercise, the user 200 can vary resistance by operating the two resistance control dials of the resistance control unit 120. The user 200 will be able to independently control movement in either direction (extensions and flexions). No matter how hard the user 200 tries to make the movements in either direction, due to applied resistance, the user 200 exerted forces will not allow him to hit harder and the speed will remain constant. As desired, in either direction the user 200 can load and unload the resistance anytime and continue to do the exercise and at the same time monitor his performance using the display unit 130. The display unit 130 will display the muscular performance of the user that can then be assessed for accommodating any suitable changes in the exercises to quicken the recovery process.

The Isokinetic exercise system or machine 100 of the present invention may be sized as 0.4 meter in length×1 meter in width, it should be understood that machine is configurable in different sizes depending upon the design changes. Further, the components, parts, assemblies and associated method of their operations, forming the system 100 described above may be replaced with substitute components that's likely to render the invention workable. The material and sizes of various components, parts, assemblies and so on described above that constitutes the present invention may vary. Further, the system 100 is sized so that it is wheel chair accessible. All of these changes should be considered falling within the scope of present disclosure.

Although some particular embodiments of the invention have been described in detail above for purposes of illustration, various modifications and enhancements are possible and can be accommodated in the embodiments without departing from the spirit and scope of the invention.

What is claimed is:

1. An isokinetic exercise and rehabilitation system (100), comprising:
   a base (102);
   a pedestal (104) configured on the base (102);
   a vertical member (106) attached to the base (102);
   a vertical column (110) slidably disposed within the pedestal (104), the vertical column (110) comprising a pivot plate (114) mounted thereon, wherein the vertical column (110) is height adjustable relative to the pedestal (104);
   a bracket (116) pivotally mounted on the pivot plate (114), the bracket (116) adapted for resting a rotary actuator (118), the rotary actuator (118) positionable at a first position parallel along an X-axis of the base (102) and a second position parallel along a Y-axis of the base (102) to enable a user to connect a selected exercising attachment (302-310) to a torque arm (128) connected to a central shaft of the rotary actuator (118) to perform an intended exercise;
   a resistance control valve unit (120) connected to the rotary actuator (118) through an intake manifold (122), the resistance control unit (120) comprising a pair of rotatable dials (120c, 120d) adapted for use by the user performing the intended exercise to rotatably set a range of resistances selectively for opposing movements in order to accommodate varying exerted forces by the user performing the intended exercise;

an electronics module (125) housing one or more angle sensors configured to detect rotational angle data and one or more pressure sensors configured to detect pressure related data in form of voltages associated with the rotary actuator (118), the electronics module (125) further configured to relay the detected voltages to an A to D converter (128) to convert the detected voltages in a digital form, which is then relayed to a display unit (130) by the A to D converter (128); and wherein the display unit (130) is configured to embody a program product for receiving and processing the detected voltages in the digital form from the A to D converter (128) to at least: generate and display a muscular performance assessment report in real-time, store the received voltages or the muscular performance assessment report for future comparison, enable printing the muscular performance assessment report, and allow the user to configure a next intended exercise.

2. The system (100) of claim 1 further comprising:
a seat (108) with handles (108a) configured over the vertical member (106) and a curved extension (104a) of the pedestal (104), wherein the seat (108) is usable to perform the intended exercise;
a bench (150) configured for use with the system (100) for performing the intended exercise and be placed either parallel along the X-axis of the base (102) or parallel along the Y-axis of the base (102), wherein the seat (108) is usable to perform the intended exercise; and
a stand (300) for removably mounting the selected exercising attachment (302-310).

3. The system (100) of claim 1 further comprising:
an insert (112) disposed within the pedestal (104) to provide a smooth slidable fitting between the vertical column (110) and the pedestal (104);
a spring loaded pop pin (104b) and a pressure disc knob (104c) operable for slidably retracting and extending the vertical column (110) in and out of the pedestal (104) to one or more heightened positions;
a locking knob (114a) and a spring loaded locking knob (114b) operable to releasably mount the bracket (116) over the pivot plate (114), wherein the locking knob (114a) and the spring loaded locking knob (114b) are further operable to rotate the bracket (116) 90 degrees; and
a gas strut (117) configured to extend or retract against a load pressure and to support up or down adjusted movement and repositioning of the vertical column (110).

4. The system (100) of claim 1, wherein the rotary actuator (118) is a vane-type rotary actuator or pump capable of rotating clockwise or anticlockwise up to 270 degrees.

5. The system (100) of claim 1, wherein the intake manifold (122) directs outputted oil from the rotary actuator (118) to a left hand aperture (120a) then to a central chamber (120e) and then out from a right hand aperture (120b) of the control valve unit (120) and vice versa.

6. The system (100) of claim 5, wherein the amount of the outputted oil flowing through the control valve unit (120) is proportional to a resistance value set by the user using the pair of rotatable dials (120c, 120d) for either of the opposing movements.

7. The system (100) of claim 3, wherein the insert (112) is made of nylon.

8. The system (100) of claim 3, wherein the vertical column (110) is locked at the one or more heightened positions by operating the spring loaded pop pin (104b), and the pressure disc knob (104c) allowing a pin of the spring loaded pop pin (104b) to get threaded into a selected aperture (110a) located on a side of the vertical column (110).

9. The system (100) of claim 1, the intended exercise is at least one of: a lower body conditioning exercise and an upper body conditioning exercise selected from a group consisting of a hip related exercise, knee related exercise, a back related exercise, a chest related exercise, a leg related exercise, a shoulder related exercise, an arm related exercise and a core exercise.

10. The system (100) of claim 1, wherein the range of resistances that can be set using the pair of rotatable dials (120c, 120d) by the user performing the intended exercise ranges from 1-10.

11. The system (100) of claim 1, wherein the bracket (116) further comprises a stabilizing handle (116a) attached thereto.

12. The system (100) of claim 11, wherein the stabilizing handle (116a) is configured for performing the intended exercise or to push or to pull the vertical column (110) during height adjustment of the vertical column (110) against a gas strut (117).

13. The system (100) of claim 1, wherein the display unit (130) is removably connected to a curved extension (104a) of the pedestal (104) using a connecting arm (132).

14. The system (100) of claim 1, wherein the electronics module (125) relays the detected voltages to the A to D converter (128) using a wired (127) or wireless connection.

15. The system (100) of claim 2, wherein the electronics module (125) relays the detected voltages to the A to D converter (128) using a wired (127) or wireless connection.

16. The system (100) of claim 1, wherein the A to D converter (128) relays the digital form of the detected voltages to the display unit (130) using a wired or wireless connection.

17. The system (100) of claim 1, wherein the program product upon receiving and processing the digital form of the detected voltages generates and displays the muscular performance assessment report of the user in the form of a user interface.

18. The system (100) of claim 17, wherein the user interface at least:
displays the opposing movements of muscles under the intended exercise in a bar graph form (134 and 136);
displays a number of reps remaining (137) in an exercise set and best extension and flexion values (138);
allows the user performing the intended exercise to at least skip the exercise set or cancel the exercise; and
displays a clock (140) representation for a rotational angle of the torque arm (126).

* * * * *